US009144626B2

(12) United States Patent
Vogt et al.

(10) Patent No.: US 9,144,626 B2
(45) Date of Patent: *Sep. 29, 2015

(54) PASTE FOR PRODUCING BONE CEMENT

(71) Applicant: Heraeus Medical GmbH, Wehrheim (DE)

(72) Inventors: Sebastian Vogt, Erfurt (DE); Hubert Büchner, Nürnberg (DE)

(73) Assignee: Heraeus Medical GmbH, Wehrheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/311,953

(22) Filed: Jun. 23, 2014

(65) Prior Publication Data

US 2014/0303275 A1   Oct. 9, 2014

Related U.S. Application Data

(63) Continuation of application No. 13/012,909, filed on Jan. 25, 2011, now Pat. No. 8,791,172.

(30) Foreign Application Priority Data

Jan. 27, 2010   (DE) .................... 10 2010 005 956

(51) Int. Cl.
*A61L 24/06* (2006.01)
*A61L 24/00* (2006.01)
*A61L 27/44* (2006.01)

(52) U.S. Cl.
CPC ......... *A61L 24/0073* (2013.01); *A61L 24/0015* (2013.01); *A61L 27/44* (2013.01); *A61L 24/06* (2013.01); *A61L 2300/00* (2013.01); *A61L 2430/02* (2013.01); *A61L 2430/24* (2013.01)

(58) Field of Classification Search
CPC ............................. A61L 24/06; A61K 6/0047
USPC ....................................................... 523/116
See application file for complete search history.

(56) References Cited

U.S. PATENT DOCUMENTS

| 3,347,954 | A |   | 10/1967 | Bredereck |         |
|-----------|---|---|---------|-----------|---------|
| 4,015,945 | A |   | 4/1977  | Frankel et al. | |
| 4,997,861 | A | * | 3/1991  | Hechenberger et al. | 523/176 |
| 6,852,775 | B1|   | 2/2005  | Soglowek et al. | |
| 8,791,172 | B2| * | 7/2014  | Vogt et al. | 523/116 |

| 2003/0086332 | A1 |   | 5/2003  | Jonsson |        |
|--------------|----|---|---------|---------|--------|
| 2003/0228973 | A1 | * | 12/2003 | Moren   | 502/150|
| 2004/0097613 | A1 |   | 5/2004  | Hecht et al. | |
| 2006/0217488 | A1 | * | 9/2006  | Renz et al. | 525/70 |
| 2008/0132603 | A1 |   | 6/2008  | Renz et al. | |
| 2009/0105144 | A1 |   | 4/2009  | Vogt et al. | |
| 2009/0105366 | A1 |   | 4/2009  | Vogt et al. | |

FOREIGN PATENT DOCUMENTS

| CA | 2267747 A1 | 9/1999 |
|----|------------|--------|
| DE | 198 18 210 A1 | 10/1999 |
| DE | 10 2007 052 116 A1 | 4/2009 |
| DE | 10 2007 050 762 B3 | 5/2009 |
| EP | 0674888 A1 | 10/1995 |
| EP | 2052747 A2 | 4/2009 |
| JP | 2003181270 A | 7/2003 |
| JP | 2004-529947 A | 9/2004 |
| JP | 2006-183013 A | 7/2006 |
| JP | 2006-257087 A | 9/2006 |

OTHER PUBLICATIONS

Office Action Issued Sep. 28, 2010 in German Appln. Ser. No. 10 2010 005 956.0.
John Charnley, "Anchorage of the Femoral Head Prosthesis to the Shaft of the Femur", The Journal of Bone and Joint Surgery, vol. 42B, No. 1, pp. 28-30, Feb. 1960.
Office Action issued Sep. 25, 2012 in CA Application No. 2,726,956.
Office Action issued Feb. 6, 2013 in AU Application No. 2011200280.
English translation of an Office Action issued Mar. 26, 2013 in JP Application No. 2011-013356.
Office Action issued May 30, 2013 in CA Application No. 2,726,956.
English translation of an Office Action issued Feb. 12, 2014 in JP Application No. 2011-013356.

* cited by examiner

*Primary Examiner* — Michael Pepitone
(74) *Attorney, Agent, or Firm* — Panitch Schwarze Belisario & Nadel LLP

(57) ABSTRACT

A paste is provided from which bone cement can be formed, which is to the largest extent possible bubble-free and has a high impact strength. The paste includes (i) 15-50 weight percent of at least one mono-functional, hydrophobic methacrylic acid ester, (ii) 40-85 weight percent of at least one filler, (iii) 0.01-4 weight percent of at least one radical initiator soluble in the methacrylic acid ester (i) and having at least one peroxide group, (iv) 0.01-4 weight percent of at least one radical initiator soluble in the methacrylic acid ester (i) and having no peroxide groups, (v) 0.000001-3 weight percent of at least one accelerator soluble in the methacrylic acid ester (i) and capable of forming radicals from the radical initiators according to (iii) and (iv), (vi) 0.001-5 weight percent of at least one halide salt, and (vii) 0.2-3 weight percent of at least one cross-linking agent.

2 Claims, No Drawings

PASTE FOR PRODUCING BONE CEMENT

This application is a Continuation of U.S. application Ser. No. 13/012,909 filed on Jan. 25, 2011, now U.S. Pat. No. 8,791,172, issued on Jul. 29, 2014, which claims the benefit of German Patent Application No. 10 2010 005 956.0 filed in Germany on Jan. 27, 2010, the entire contents of which are hereby incorporated by reference.

BACKGROUND OF THE INVENTION

The present invention relates to a kit for the production of bone cement, a paste for the production of bone cement, and uses of the kit and the paste.

Bone cements based on poly(methyl methacrylate) (PMMA) have been known for decades and trace back to the basic work done by Sir Charnley (Charnley, J., "Anchorage of the femoral head prosthesis of the shaft of the femur," *J. Bone Joint Surg.* 42: 28-30 (1960)). In principle, the basic configuration of the PMMA bone cements has remained the same since then. PMMA bone cements comprise a fluid monomer component and a powder component. The monomer component includes, in general, the monomer methyl methacrylate and an activator (for example, N,N-dimethyl-p-toluidine) dissolved in this monomer. The powder component comprises one or more polymers produced by polymerization, preferably suspension polymerization, based on methyl methacrylate and comonomers, such as styrene, methyl acrylate, or similar monomers, a radiopaque material, and the initiator (for example, dibenzoyl peroxide). When the powder component is mixed with the monomer component, due to the swelling of the polymers of the powder component in the methyl methacrylate, a plastically deformable paste is produced. Simultaneously, the activator N,N-dimethyl-p-toluidine reacts with the dibenzoyl peroxide, which breaks down with the formation of radicals. The formed radicals initiate the radical polymerization of the methyl methacrylate. With advancing polymerization of the methyl methacrylate, the viscosity of the cement paste increases until the paste solidifies and is thus cured.

The basic mechanical requirements on PMMA bone cements, such as 4-point flexural strength, flexural modulus, and compression strength, are described in ISO 5833. For the person applying the PMMA bone cement, the property of non-adhesiveness of the bone cement is of significant importance. The term "non-adhesiveness" is defined in ISO 5833. For conventional PMMA bone cements, non-adhesiveness indicates that the cement has reached the workable phase after the mixing of the components due to the swelling of the polymers contained in the cement powder in the monomer. Basically, a PMMA bone cement must be non-adhesive, so that the user can form and apply the cement. The PMMA bone cement must not adhere to gloves and application aids, such as mixing systems, crucibles, or spatulas.

The significant disadvantage of the previous PMMA bone cements for the medical user consists in that the user must mix the liquid monomer component with the powder component in a mixing system or in crucibles directly before the application of the cement. Here, mixing errors can easily occur, which could negatively affect the cement quality. The mixing must be performed in an uninterrupted process. Here, it is important that the entire cement powder be mixed with the monomer component without the formation of clumps and that during the mixing process the entry of air bubbles be avoided. With the use of vacuum mixing systems, in contrast to hand mixing, the formation of air bubbles in the cement paste is largely prevented, but an additional vacuum pump is required for these systems. Examples of mixing systems are disclosed in the publications: U.S. Pat. No. 4,015,945, European patent application publication EP 0 674 888 A1, and Japanese patent application publication (Kokai) JP 2003/181270 A. Vacuum mixing systems and vacuum pumps are relatively expensive. After the mixing of the monomer component with the powder component, depending on the type of the cement, a more or less long time must elapse until the cement paste is non-adhesive and can be applied. Due to the many possible errors in the mixing of conventional PMMA bone cements, appropriately trained personnel are needed. The training entails not insignificant costs. Furthermore, the mixing of the fluid monomer component with the powder component leads to an exposure of the user to monomer vapors and to the release of powdery cement particles.

In order to prevent these conditions during the production of a bone cement from a fluid monomer solution and a polymer powder, German Patent DE 10 2007 050 762 B3 proposes a paste-like bone cement. This paste-like bone cement is based on the idea of dissolving a polymer in a methacrylate monomer and suspending in this solution a particulate polymer not soluble in the methacrylate monomer. In this way, it is possible to produce a paste-like mass that exhibits high inner cohesion due to the dissolved polymer and has high viscosity due to the particulate, non-soluble polymer, so that the paste can temporarily withstand the bleeding pressure. Due to radical polymerization of the methacrylate monomers, the paste can be cured. The radical polymerization is possible with (i) a radical initiator, such as barbituric acid derivatives or dibenzoyl peroxide, and (ii) a copper salt as the activator. It has been shown, however, that with the use of this initiator system, the formed bone-cement paste does not cure uniformly, but instead from the core outward in the direction of the surface of the formed bone-cement paste. Due to the evaporation of the monomer contained in the bone-cement paste, bubbles are formed in the resulting bone cement. Furthermore, it has been observed that with the use of this initiator system, the monomers contained in the bone-cement paste are not completely converted. These circumstances have a disadvantageous effect on the physical properties of the bone cement, in particular on the impact strength.

BRIEF SUMMARY OF THE INVENTION

The invention is therefore based on the object of providing a kit that allows the production of bone cement that is bubble-free to the greatest extent possible with high impact strength. Another object consists in providing a paste from which bone cement can be formed that is bubble-free to the greatest extent and exhibits a high impact strength.

The first object is achieved according to the invention by providing a kit comprising:

a kit component (a), which contains as components at least (a1) a mono-functional, hydrophobic methacrylic acid ester, (a2) a filler, and (a3) a radical initiator soluble in (a1) and having at least one peroxide group, wherein kit component (a) contains 15-85 weight percent methacrylic acid ester (a1) and less than 85 weight percent fillers (a2), based on the total weight of the components contained in kit component (a), a kit component (b), which contains as components at least (b1) a mono-functional, hydrophobic methacrylic acid ester, (b2) a filler, and (b3) a radical initiator soluble in (b1) and having no peroxide group, wherein kit component (b) contains 15-85 weight percent methacrylic acid ester (b1) and less than 85 weight percent fillers (b2), based on the total weight of the components contained in kit component (b), a kit component (c), which contains as components at least (c1) a mono-functional, hydrophobic methacrylic acid ester, (c2) a filler, and (c3) an accelerator soluble in (c1) and capable of forming radicals from the radical initiators (a3) and (b3), wherein kit component (c) contains 15-85 weight percent methacrylic acid ester (c1) and less than 85 weight percent fillers (c2), based on the total weight of the components contained in kit component (c), wherein at least one of the kit components (a), (b), or (c) contains at least one halide salt, wherein at least one of the kit components (a), (b), or (c) contains at least one cross-linking agent, and wherein, based on the total weight of the components contained in the kit components (a), (b), and (c), (i) the total weight percentage of the methacrylic acid esters (a1), (b1), and (c1) lies in the range of 15-50 weight percent, (ii) the total weight percentage of the fillers (a2), (b2), and (c2) lies in the range of 40-85 weight percent, (iii) the weight percentage of the radical initiator (a3) lies in the range of 0.01-4 weight percent, (iv) the weight percentage of the radical initiator (b3) lies in the range of 0.01-4 weight percent, (v) the weight percentage of the accelerator (c3) lies in the range of 0.000001-3 weight percent, (vi) the total weight percentage of the at least one halide salt lies in the range of 0.001-5 weight percent, and (vii) the total weight percentage of the at least one cross-linking agent lies in the range of 0.2-3 weight percent.

Furthermore, the second object is achieved according to the invention by providing a paste comprising:

(i) 15-50 weight percent of at least one mono-functional, hydrophobic methacrylic acid esters, (ii) 40-85 weight percent of at least one filler, (iii) 0.01-4 weight percent of at least one radical initiator soluble in the methacrylic acid ester (i) and having at least one peroxide group, (iv) 0.01-4 weight percent of at least one radical initiator soluble in the methacrylic acid ester (i) and having no peroxide group, (v) 0.000001-3 weight percent of at least one accelerator soluble in the methacrylic acid ester (i) and capable of forming radicals from the radical initiators according to (iii) and (iv), (vi) 0.001-5 weight percent of at least one halide salt, and (vii) 0.2-3 weight percent of at least one cross-linking agent.

Through the combination of the system, according to the invention, of radical initiators that are different from each other and the accelerator, on one hand, as well as the cross-linking agent, on the other hand, the production of a nearly bubble-free bone cement with high impact strength, which reaches its final strength within a few minutes, is possible.

If, as known from DE 10 2007 050 762 B3, for the polymerization of the monomers contained in the bone-cement paste, either a barbituric acid derivative or a peroxide together with a copper salt is used as the initiator, then this leads to a reduction of the impact strength due to the formation of bubbles and incomplete conversion of the monomers contained in the bone-cement paste.

Surprisingly, it was found that the impact strength of the bone cement can be increased if, on one hand, an initiator system is used which contains at least one radical initiator having a peroxide group, a radical initiator having no peroxide group, as well as a suitable accelerator and, on the other hand, the polymerization takes place in the presence of a defined concentration of a cross-linking agent.

These effects are possibly traced back to the fact that, due to the use of the radical initiator having no peroxide group, it leads to a quick onset of the polymerization and a uniform heating. In connection therewith, solidification sets in when post-curing is initiated by the radical initiator containing at least one peroxide group. This post-curing is accompanied by a strong thermal shock. Furthermore, it appears to lead to a reaction between the two different radical initiators with the result that the polymerization process is performed completely. Due to the simultaneous presence of the cross-linking agent, this leads to a massive increase in viscosity setting in during an early stage of the curing.

According to the invention, it is essential that the redox initiator having at least one peroxide group is separated from the redox initiator having no peroxide group before the mixing of the kit components. If both redox initiators were present together in one kit component, then this would lead to the formation of radicals due to a reaction between the two redox initiators and thus to an undesired polymerization of the monomers present, so that these kit components would not be stable for storage. Thus, at least three kit components are required that contain the following components separate from each other: (i) a redox initiator having a peroxide group, (ii) a redox initiator having no peroxide group, and (iii) an accelerator.

Thus, according to the invention, a kit is provided. In the scope of the invention, a kit is understood to be a system having several separately packaged kit components. The individual kit components can be provided, for example, packaged in a sterile way in bottles or bags.

DETAILED DESCRIPTION OF THE INVENTION

In the present case, the kit comprises at least the three kit components (a), (b), and (c) that contain different components and thus have different compositions. It is also possible according to the invention that the kit contain more than three kit components. By mixing the compositions contained in the at least three kit components, initially a paste can be produced, which finally can be shaped by the user, in order to form bone cement after the curing.

Kit component (a) contains as components at least (a1) a mono-functional, hydrophobic methacrylic acid ester, (a2) a filler, and (a3) a radical initiator soluble in (a1) and having at least one peroxide group, wherein kit component (a) contains 15-85 weight percent methacrylic acid ester (a1) and less than 85 weight percent of the fillers (a2), based on the total weight of the components contained in kit component (a).

In addition, kit component (a) could comprise additional components. It is also possible, however, that kit component (a) consists of the components named above.

Any hydrophobic ester of methacrylic acid can be used as the mono-functional, hydrophobic methacrylic acid ester (a1).

Through the use of hydrophobic, mono-functional methacrylic acid esters (a1), a later increase in volume of the bone cement and thus damage to the bone can be prevented. According to a preferred embodiment, the mono-functional methacrylic acid ester (a1) is hydrophobic, when it contains, besides the ester group, no additional polar groups. Preferably, the mono-functional, hydrophobic methacrylic acid ester (a1) has no carboxyl groups, hydroxyl groups, amide groups, sulfonic acid groups, sulfate groups, phosphate groups, or phosphonate groups.

The methacrylic acid esters (a1) used according to the invention preferably have a weight average molecular weight of less than 1000 g/mol.

In the scope of the invention, data on the molecular weight refer to the viscometrically determined molecular weight.

The ester used is preferably an alkyl ester. According to a preferred embodiment, the alkyl esters are esters of methacrylic acid with alcohols having 1-20 carbon atoms, more preferred 1-10 carbon atoms, even more preferred 1-6 carbon atoms, and very especially preferred 1-4 carbon atoms. The alcohols can be substituted or unsubstituted and are preferably unsubstituted. Furthermore, the alcohols can be saturated or unsaturated and are preferably saturated.

According to an especially preferred embodiment, the mono-functional, hydrophobic methacrylic acid ester (a1) comprises methacrylic acid methyl ester or methacrylic acid ethyl ester.

Kit component (a) contains 15-85 weight percent, preferably 20-70 weight percent, more preferred 25-60 weight percent, and even more preferred 25-50 weight percent of at least one mono-functional, hydrophobic methacrylic acid ester (a1), based on the total weight of the components contained in kit component (a). Consequently, kit component (a) can contain one or more structurally different, mono-functional, hydrophobic methacrylic acid esters (a1), as long as the total weight of the mono-functional, hydrophobic methacrylic acid esters (a1) lies in the specified range.

The at least one filler (a2) contained in kit component (a) is a material that is solid at room temperature and is capable of increasing the viscosity of the mixture composed of the other components in kit component (a). The filler (a2) must be biocompatible.

According to a preferred embodiment, the filler (a2) is selected from the group consisting of (i) polymers soluble in at least the or one of the methacrylic acid esters (a1), (b1), and (c1), more preferred polymers soluble in at least the or one of the methacrylic acid esters (a1), (ii) polymers insoluble in at least the or one of the methacrylic acid esters (a1), (b1), and (c1), more preferred polymers insoluble in at least the or one of the methacrylic acid esters (a1), (iii) inorganic salts, (iv) inorganic oxides, (v) metals, and (vi) metal alloys. The filler (a2) is preferably particulate. According to an especially preferred embodiment, the filler (a2) has an average particle size in the range from 10 nm-100 μm and especially preferred in the range from 100 nm-10 μm. As used herein, average particle size is understood to be a range of sizes assumed by at least 90 percent of the particles.

In the scope of the invention, the term "polymers" includes both homopolymers and copolymers.

The polymer soluble in at least one of the methacrylic acid esters (a1), (b1), and (c1) preferably comprises a polymer having a weight average molecular weight of at least 150,000 g/mol. For example, the polymer could comprise a polymer or copolymer of a methacrylic acid ester. According to an especially preferred embodiment, the at least one polymer is selected from the group consisting of polymethacrylic acid methyl ester (PMMA), polymethacrylic acid ethyl ester (PMAA), polymethacrylic acid propyl ester (PMAP), polymethacrylic acid isopropyl ester, and polymethyl-co-acrylic methacrylate.

The polymer insoluble in at least one of the methacrylic acid esters (a1), (b1), and (c1) comprises, for example, polyethylene, polypropylene, or polybutadiene. The polymer insoluble in at least one of the methacrylic acid esters (a1), (b1), and (c1) can be cross-linked or not cross-linked.

The inorganic salt usable as filler (a2) can be a salt soluble or insoluble in the methacrylic acid ester (a1). Preferably, the inorganic salt comprises a salt of an element selected from the 2nd main group of the Periodic Table of the elements. According to a preferred embodiment, the inorganic salt is a salt of calcium, strontium, or barium. According to an especially preferred embodiment, the inorganic salt is calcium sulfate, barium sulfate, or calcium carbonate.

The inorganic oxide usable as filler (a2) can preferably be a metal oxide. According to a preferred embodiment, the inorganic oxide is an oxide of the transition metals. According to an especially preferred embodiment, the inorganic oxide comprises titanium dioxide or zirconium dioxide.

The metal usable as filler (a2) can comprise, for example, a transition metal. According to a preferred embodiment, the metal is tantalum or tungsten.

The metal alloy usable as filler (a2) is an alloy of at least two metals. Preferably, the alloy contains at least one transition metal. According to an especially preferred embodiment, the alloy contains at least tantalum or tungsten. The alloy could also comprise an alloy made of tantalum or tungsten.

The percentage of the at least one filler (a2) equals less than 85 weight percent, preferably less than 80 weight percent, and more preferred less than 75 weight percent, based on the total weight of the components contained in kit component (a). Preferably, kit component (a) contains 15-84.99 weight percent, more preferred 15-80 weight percent, and even more preferred 20-75 weight percent of the at least one filler (a2), based on the total weight of the components contained in kit component (a). Accordingly, component (a) can contain one or more structurally different fillers (a2) as long as the total weight of the fillers (a2) lies in the specified range.

Component (a) also contains a radical initiator (a3) soluble in the mono-functional, hydrophobic methacrylic acid ester (a1) and having at least one peroxide group. Although used in singular form here, according to the invention the term "radical initiator (a3)" also extends to a plurality of structurally different radical initiators (a3).

As used herein, radical initiator (a3) is understood to be a compound from which a radical can be formed by the action of the accelerator (c3), wherein this radical is capable of triggering the polymerization of the methacrylic acid ester (a1), (a2), and (a3). The radical initiator (a3) thus comprises a radical polymerization starter.

In the presence of the accelerator (c3), the radical initiator (a3) has a decomposition rate different from the radical initiator (b3). According to an especially preferred embodiment, in the presence of the accelerator (c3), the radical initiator (a3) has a lower decomposition rate than the radical initiator (b3).

According to a preferred embodiment, the solubility of the radical initiator (a3) in the methacrylic acid ester (a1) equals at least 0.5 weight percent, based on the weight of the methacrylic acid ester (a1).

According to an especially preferred embodiment, the radical initiator (a3) is selected from the group consisting of dibenzoyl peroxide and dilauroyl peroxide.

Component (a) contains preferably 0.01-12 weight percent, preferably 0.01-10 weight percent, more preferred 0.05-8 weight percent, and even more preferred 0.05-5 weight percent of at least one radical initiator (a3), based on the total weight of the components contained in kit component (a).

Kit component (b) contains as components at least (b1) a mono-functional, hydrophobic methacrylic acid ester, (b2) a filler, and (b3) a radical initiator soluble in (b1) and having no peroxide group, wherein kit component (b) contains 15-85 weight percent methacrylic acid esters (b1) and less than 85 weight percent of filler (b2), based on the total weight of the components contained in kit component (b). In addition, component (b) can comprise additional components. However, it is also possible that component (b) consists of the components mentioned above.

Any hydrophobic ester of methacrylic acid can be used as the mono-functional, hydrophobic methacrylic acid ester (b1).

Through the use of hydrophobic, mono-functional methacrylic acid esters (b1), a later increase in volume of the bone cement and thus damage to the bone can be prevented. According to a preferred embodiment, the mono-functional methacrylic acid ester (b1) is hydrophobic, if it has, in addition to the ester group, no other polar groups. Preferably, the mono-functional, hydrophobic methacrylic acid ester (b1) contains no carboxyl groups, hydroxyl groups, amide groups, sulfonic acid groups, sulfate groups, phosphate groups, or phosphonate groups.

The methacrylic acid esters (b1) used according to the invention preferably have a weight average molecular weight of less than 1000 g/mol.

The esters preferably comprise alkyl esters. According to a preferred embodiment, the alkyl esters are esters of methacrylic acid with alcohols having 1-20 carbon atoms, more preferred 1-10 carbon atoms, even more preferred 1-6 carbon atoms, and very especially preferred 1-4 carbon atoms. The alcohols can be substituted or unsubstituted and are preferably unsubstituted. The alcohols can further be saturated or unsaturated and are preferably saturated.

According to an especially preferred embodiment, the mono-functional, hydrophobic methacrylic acid ester (b1) comprises methacrylic acid methyl ester or methacrylic acid ethyl ester.

Kit component (b) contains 15-85 weight percent, preferably 20-70 weight percent, more preferred 25-60 weight percent, and even more preferred 25-50 weight percent of at least one mono-functional, hydrophobic methacrylic acid ester (b1), based on the total weight of the components contained in kit component (b). Accordingly, kit component (b) can contain one or more structurally different mono-functional, hydrophobic methacrylic acid esters (b1) as long as the total weight of the mono-functional, hydrophobic methacrylic acid ester (b1) lies in the specified range.

The at least one filler (b2) contained in kit component (b) comprises a material that is solid at room temperature and is capable of increasing the viscosity of the mixture composed of the other components contained in kit component (b). The filler (b2) must be biocompatible.

According to a preferred embodiment, the filler (b2) is selected from the group consisting of (i) polymers soluble in at least the or one of the methacrylic acid esters (a1), (b1), and (c1), more preferred polymers soluble in at least the or one of the methacrylic acid esters (b1), (ii) polymers insoluble in at least the or one of the methacrylic acid esters (a1), (b1), and (c1), more preferred polymers insoluble in at least the or one of the methacrylic acid esters (b1), (iii) inorganic salts, (iv) inorganic oxides, (v) metals, and (vi) metal alloys.

The polymer soluble in at least one of the methacrylic acid esters (a1), (b1), and (c1) preferably comprises a polymer having a weight average molecular weight of at least 150,000 g/mol. For example, the polymer can comprise a polymer or copolymer of a methacrylic acid ester. According to an especially preferred embodiment, the at least one polymer is selected from the group consisting of polymethacrylic acid methyl ester (PMMA), polymethacrylic acid ethyl ester (PMAA), polymethacrylic acid propyl ester (PMAP), polymethacrylic acid isopropyl ester, and polymethyl-co-acrylic methacrylate.

The polymer insoluble in at least one of the methacrylic acid esters (a1), (b1), and (c1) comprises, for example, polyethylene, polypropylene, or polybutadiene. The polymer insoluble in at least one of the methacrylic acid esters (a1), (b1), and (c1) can be cross-linked or not cross-linked.

The inorganic salt usable as filler (b2) can be a salt soluble or insoluble in the methacrylic acid ester (b1). Preferably, the inorganic salt comprises a salt of an element selected from the 2nd main group of the periodic table of the elements. According to a preferred embodiment, the inorganic salt is a salt of calcium, strontium, or barium. According to an especially preferred embodiment, the inorganic salt is calcium sulfate, barium sulfate, or calcium carbonate.

The inorganic oxide usable as filler (b2) can preferably comprise a metal oxide. According to a preferred embodiment, the inorganic oxide is an oxide of the transition metals. According to an especially preferred embodiment, the inorganic oxide comprises titanium oxide or zirconium dioxide.

The metal usable as filler (b2) can comprise, for example, a transition metal. According to a preferred embodiment, the metal is tantalum or tungsten.

The metal alloy usable as filler (b2) is an alloy of at least two metals. Preferably, the alloy contains at least one transition metal. According to an especially preferred embodiment, the alloy contains at least tantalum or tungsten. The alloy can also comprise an alloy made of tantalum and tungsten.

The percentage of the at least one filler (b2) equals less than 85 weight percent, preferably less than 80 weight percent, and more preferred less than 75 weight percent, based on the total weight of the components contained in kit component (b). Preferably, kit component (b) contains 15-84.99 weight percent, more preferred 15-80 weight percent, and even more preferred 20-75 weight percent of the at least one filler (b2), based on the total weight of the components contained in kit component (b). Accordingly, component (b) can contain one or more structurally different fillers (b2), as long as the total weight of the fillers (b2) lies in the specified range.

Component (b) also contains a radical initiator (b3) soluble in the mono-functional, hydrophobic methacrylic acid ester (b1) and has no peroxide group. Although used here in the singular form, according to the invention the term "radical Initiator (b3)" also extends to a plurality of structurally different radical initiators (b3).

As used herein, radical initiator (b3) is understood to be a compound from which a radical can be formed by action of the accelerator (c3), wherein this compound is capable of triggering the polymerization of the methacrylic acid esters (b1), (b2), and (b3). The radical initiator (b3) thus comprises a radical polymerization starter.

In the presence of the accelerator (c3), the radical initiator (b3) has a decomposition rate that is different from the radical initiator (a3). According to an especially preferred embodiment, in the presence of the accelerator (c3), the radical initiator (b3) has a higher decomposition rate than the radical initiator (a3).

According to a preferred embodiment, the solubility of the radical initiator (b3) in the methacrylic acid ester (b1) equals at least 0.5 weight percent, based on the weight of the methacrylic acid ester (b1).

The radical initiator (b3) preferably comprises barbituric acid or barbituric acid derivatives, in which the barbituric acid carries a substitute on at least one of the positions 1 or 5. Such barbituric acid derivatives have the advantage that they exhibit no pharmacological action.

According to the invention, the barbituric acid derivative is preferably mono-substituted. According to a preferred embodiment, a barbituric acid substituted at position 5 is used as the radical initiator (b3). The substituent of the barbituric acid derivatives furthermore preferably comprises a hydrophobic substituent. Preferably, the barbituric acid derivative comprises an alkyl, cycloalkyl, or aryl derivative of the barbituric acid.

According to an especially preferred embodiment, the barbituric acid derivative is selected from the group consisting of cyclohexyl barbituric acid, 1,3,5-trimethyl barbituric acid, 1-phenyl-5-benzyl barbituric acid, 1-benzyl-5-phenyl barbituric acid, 1,3-dimethyl barbituric acid, 1,3-dimethyl-5-phenyl barbituric acid, 1-cyclohexyl-5-ethyl barbituric acid, 5-lauryl barbituric acid, 1-n-butyl-barbituric acid, 5-n-butyl barbituric acid, 5-allyl barbituric acid, 5-hydroxy-5-butyl barbituric acid, 5,5-dibromo barbituric acid, trichloro barbituric acid, 5-nitro barbituric acid, 5-amino barbituric acid, 5-hydroxy barbituric acid, and 5,5-dihydroxy barbituric acid.

Under a very especially preferred embodiment, the barbituric acid derivative is selected from the group consisting of 1-cyclohexyl-5-ethyl-barbituric acid, 1-n-butyl-barbituric acid, and 5-n-butyl-barbituric acid.

According to the invention, the term "barbituric acid derivatives" also includes alkaline earth salts and alkali salts of these barbituric acid derivatives.

Kit component (b) preferably contains 0.01-12 weight percent, preferably 0.01-8 weight percent, more preferred 0.05-6 weight percent, and even more preferred 0.05-5 weight percent of at least one radical initiator (b3), based on the total weight of the components contained in kit component (b). Accordingly, kit component (b) can contain one or more structurally different radical initiators (b3), as long as the total weight of the radical initiator (b3) lies in the specified range.

Kit component (b) [sic (c)] contains as components at least (c1) a mono-functional, hydrophobic methacrylic acid ester, (c2) a filler, and (c3) an accelerator soluble in (c1) and is capable of forming radicals from the radical initiators (a3) and (b3), wherein kit component (c) has 15-85 weight percent methacrylic acid ester (c1), and less than 85 weight percent of filler (c2) based on the total weight of the components contained in kit component (c).

Any hydrophobic esters of methacrylic acid can be used as the mono-functional, hydrophobic methacrylic acid ester (c1).

Through the use of hydrophobic, mono-functional methacrylic acid esters (c1), a later increase in volume of the bone cement and thus damage to the bone can be prevented. According to a preferred embodiment, the mono-functional methacrylic acid ester (c1) is hydrophobic, if it has, besides the ester group, no other polar groups. Preferably the mono-functional, hydrophobic methacrylic acid ester (c1) has no carboxyl groups, hydroxyl groups, amide groups, sulfonic acid groups, sulfate groups, phosphate groups, or phosphonate groups.

The methacrylic acid esters (c1) used according to the invention preferably have a weight average molecular weight of less than 1000 g/mol.

The esters preferably comprise alkyl esters. According to a preferred embodiment, the alkyl esters are esters of methacrylic acid with alcohols having 1-20 carbon atoms, more preferred 1-10 carbon atoms, even more preferred 1-6 carbon atoms, and very especially preferred 1-4 carbon atoms. The alcohols can be substituted or unsubstituted and are preferably unsubstituted. The alcohols furthermore can be saturated or unsaturated and are preferably saturated.

According to an especially preferred embodiment, the mono-functional, hydrophobic methacrylic acid ester (c1) comprises methacrylic acid methyl ester or methacrylic acid ethyl ester.

Kit component (c) contains 15-85 weight percent, preferably 20-70 weight percent, more preferred 25-60 weight percent, and even more preferred 25-50 weight percent of at least one mono-functional, hydrophobic methacrylic acid ester (c1), based on the total weight of the components contained in kit component (c). Accordingly, kit component (c) can contain one or more structurally different, mono-functional, hydrophobic methacrylic acid esters (c1), as long as the total weight of the mono-functional, hydrophobic methacrylic acid esters (c1) lies in the specified range.

The at least one filler (c2) contained in kit component (c) comprises a material that is solid at room temperature and is capable of increasing the viscosity of the mixture composed of the other components contained in kit component (c). The filler (c2) must be biocompatible.

According to a preferred embodiment, the filler (c2) is selected from the group consisting of (i) polymers soluble in at least the or one of the methacrylic acid esters (a1), (b1), and (c1), more preferred polymers soluble in at least the or one of the methacrylic acid esters (1), (ii) polymers insoluble in at least the or one of the methacrylic acid esters (a1), (b1), and (c1), more preferred polymers insoluble in at least the or one of the methacrylic acid esters (c1), (iii) inorganic salts, (iv) inorganic oxides, (v) metals, and (vi) metal alloys.

The polymer soluble in at least one of the methacrylic acid esters (a1), (b1), and (c1) preferably comprises a polymer having a weight average molecular weight of at least 150,000 g/mol. For example, the polymer can comprise a polymer or copolymer of a methacrylic acid ester. According to an especially preferred embodiment, the at least one polymer is selected from the group consisting of polymethacrylic acid methyl ester (PMMA), polymethacrylic acid ethyl ester (PMAA), polymethacrylic acid propyl ester (PMAP), polymethacrylic acid isopropyl ester, and polymethyl-co-acrylic methacrylate.

The polymer insoluble in at least one of the methacrylic acid esters (a1), (b1), and (c1) comprises, for example, polyethylene, polypropylene, or polybutadiene. The polymer insoluble in at least one of the methacrylic acid esters (a1), (b1), and (c1) can be cross-linked or not cross-linked.

The inorganic salt usable as filler (c2) can be a salt soluble or insoluble in the methacrylic acid ester (c1). Preferably the inorganic salt comprises a salt of an element selected from the 2nd main group of the periodic table of the elements. According to a preferred embodiment, the inorganic salt is a salt of calcium, strontium, or barium. According to an especially preferred embodiment, the inorganic salt is calcium sulfate, barium sulfate, or calcium carbonate.

The inorganic oxide usable as filler (c2) preferably can comprise a metal oxide. According to a preferred embodiment, the inorganic oxide is an oxide of the transition metals. According to an especially preferred embodiment, the inorganic oxide comprises titanium dioxide or zirconium dioxide.

The metal usable as filler (c2) can comprise, for example, a transition metal. According to a preferred embodiment, the metal is tantalum or tungsten.

The metal alloy usable as filler (c2) is an alloy of at least two metals. Preferably, the alloy contains at least one transition metal. According to an especially preferred embodiment, the alloy contains at least tantalum or tungsten. The alloy can also comprise an alloy made of tantalum and tungsten.

The percentage of the at least one filler (c2) equals less than 85 weight percent, preferably less than 80 weight percent, and more preferred less than 75 weight percent, based on the total weight of the components contained in kit component (c). Preferably, kit component (c) contains 15-84.99 weight percent, more preferred 15-80 weight percent, and even more preferred 20-75 weight percent of the at least one filler (c2), based on the total weight of the components contained in kit component (c). Accordingly, component (c) can contain one or more structurally different fillers (c2), as long as the total weight of the fillers (c2) lies in the specified range.

Kit component (c) also contains an accelerator (c3) soluble in the mono-functional, hydrophobic methacrylic acid ester (c1) and is capable of forming radicals from the radical initiators (a3) and (b3). Although used here in singular form, according to the invention the term "accelerator (c3)" also extends to a plurality of structurally different accelerators (c3).

According to a preferred embodiment, the solubility of the accelerator (c3) in the methacrylic acid ester (c1) equals at least 0.5 weight percent, based on the weight of the methacrylic acid ester (c1).

According to the invention, accelerators capable of forming radicals from the radical initiators (a3) and (b3) are understood to be compounds that can convert the radical initiators (a3) and (b3) to radicals, optionally in the presence of additional compounds contained in the kit according to the invention, as for example halide ions. Such accelerators are well known from the prior art.

The accelerator (c3) preferably comprises a salt having ions of metals that can assume, besides the oxidation stage 0, at least two additional oxidation stages. According to an especially preferred embodiment, the metal ions are selected from the group consisting of copper ions, iron ions, cobalt ions, and manganese ions. Accordingly, an iron salt, a cobalt salt, or a manganese salt is used as the accelerator (c3). According to one very especially preferred embodiment, the accelerator (c3) is selected from the group consisting of copper(II)-2-ethylhexanoate, copper(II)-laurate, copper(II)-decanoate, copper(II)-octoate, copper(II) acetylacetonate, and copper (II)-methacrylate.

Kit component (c) preferably contains 0.00001-12 weight percent, preferably 0.0001-9 weight percent, more preferred 0.001-6 weight percent, and even more preferred 0.05-5 weight percent of at least one accelerator (c3), based on the total weight of the components contained in kit component (c). Accordingly, kit component (c) can contain one or more structurally different accelerators (c3), as long as the total weight of the accelerator (c3) lies in the specified range.

At least one of the kit components (a), (b), or (c) further contains a halide salt. The halide salt preferably comprises a halide salt soluble in at least one of the methacrylic acid esters (a1), (b1), and (c1). Preferably, the halide salt is soluble in at least one of the methacrylic acid esters (a1), (b1), and (c1), with which the halide salt is present together in the kit component.

According to a preferred embodiment, the solubility of the halide salt in at least one of the methacrylic acid esters (a1), (b1), and (c1) equals at least 0.5 weight percent, based on the weight of the at least one methacrylic acid ester (a1), (b1), and (c1).

According to the invention, halide salts are understood to be salts that contain at least one type of halide ion and dissociate in at least one of the methacrylic acid esters (a1), (b1), and (c1). Preferably, the halide ions comprise chloride ions or bromide ions, very preferred chloride ions. According to the invention, preferably metal halides, hydrochlorides, and quaternary ammonium halide salts can be used as the halide salts.

According to an especially preferred embodiment, the halide salt is selected from the group consisting of copper(II)-chloride, copper(II)-bromide, iron(III)-chloride, iron(III)-bromide, cobalt(II)-chloride, cobalt(II)-bromide, triethylamine hydrochloride, triethylamine hydrobromide, propylamine hydrochloride, butylamine hydrochloride, methacryloyl choline chloride, methyltrioctylammonium chloride, and triethyl benzyl ammonium chloride.

The percentage of the at least one halide salt in at least one of the kit components (a), (b), or (c) preferably equals 0.002-10 weight percent, preferably 0.002-7 weight percent, and more preferred 0.003-6 weight percent, based on the total weight of the components contained in this at least one kit component.

Furthermore, at least one of the kit components (a), (b), or (c) contains a cross-linking agent. The cross-linking agent comprises a bi-functional or tri-functional compound. According to the invention, the cross-linking agent should cause a cross-linking of the polymerizing, mono-functional, hydrophobic methacrylic acid ester during the curing of the bone cement.

According to a preferred embodiment, the cross-linking agent has at least two acrylate groups. Especially preferred, the cross-linking agent is selected from the group consisting of ethylene glycol dimethacrylate, butylene glycol dimethacrylate (e.g., butane-1,4-diol-dimethacrylate), and hexamethylene dimethacrylate (e.g., hexane-1,6-diol-dimethacrylate).

The percentage of the at least one cross-linking agent preferably equals 0.3-10 weight percent, preferably 0.4-8 weight percent, and more preferred 0.5-6 weight percent, based on the total weight of the components contained in this at least one kit component.

The kit according to the invention can furthermore contain at least one pharmaceutical substance. The pharmaceutical substance can preferably be selected from the group consisting of antibiotics, anti-inflammatory agents, hormones, growth factors, bisphosphonates, and cytostatic agents.

The at least one antibiotic is preferably selected from the group consisting of gentamicin sulfate, gentamicin hydrochloride, amikacin sulfate, amikacin hydrochloride, tobramycin sulfate, tobramycin hydrochloride, clindamycin hydrochloride, lincosamine hydrochloride, moxifloxacin, ciprofloxacin, teicoplanin, vancomycin, ramoplanin, metronidazole, tinidazole, and omidazole.

The at least one anti-inflammatory agent is preferably selected from the group consisting of non-steroidal anti-inflammatory agents and glucocorticoids. According to an especially preferred embodiment, the at least one anti-inflammatory agent is selected from the group consisting of acetylsalicylic acid, ibuprofen, diclofenac, ketoprofen, dexamethasone, prednisone, hydrocortisone, hydrocortisone acetate, and fluticasone.

The at least one hormone is preferably selected from the group consisting of serotonin, somatotropin, testosterone, and estrogen.

The at least one growth factor is preferably selected from the group consisting of the Fibroblast Growth Factor (FGF), Transforming Growth Factor (TGF), Platelet Derived Growth Factor (PDGF), epidermal growth factor (EGF), Vascular Endothelial Growth Factor (VEGF), insulin-like growth factors (IGF), Hepatocyte Growth Factor (HGF), interleukin-1B, interleukin 8, and nerve growth factor.

The at least one cytostatic agent is preferably selected from the group consisting of alkylating agents, platinum analogs, intercalating agents, mitotic inhibitors, taxanes, topoisomerase inhibitors, and antimetabolites.

The at least one bisphosphonate is preferably selected from the group consisting of zoledronate and aledronate.

The at least one pharmaceutical substance can be contained in one or more of the kit components (a), (b), and (c).

According to the invention, the kit can further have a radiopaque material. The radiopaque material is preferably selected from the group consisting of zirconium dioxide, barium sulfate, and tantalum. The at least one radiopaque material can be contained in one or more of the kit components (a), (b), and (c).

According to the invention, the kit can further contain at least one dye. Especially preferred, the dye can comprise a food coloring. According to an especially preferred embodiment, chlorophyllin (E141), riboflavin, and/or lissamine green is used as the dye. The at least one dye can be contained in one or more of the kit components (a), (b), and (c).

The kit can also contain at least one stabilizer. The stabilizer should be suitable for preventing spontaneous polymerization of the monomers contained in the kit components (a), (b), and (c). Furthermore, the stabilizer should exhibit no disruptive interactions with the other components contained in the kit components. Such stabilizers are known from the prior art. According to a preferred embodiment, the stabilizer comprises 2,6-di-tert-butyl-4-methylphenol and/or 2,6-di-tert-butyl-phenol.

The at least one stabilizer can be contained in one or more of the kit components (a), (b), and (c) and is preferably contained in each of the three kit components (a), (b), and (c).

In addition, the kit can optionally have additional additives.

Due to the defined weight percentages of methacrylic acid esters (a1), (b1), and (c1) and fillers (a2), (b2), and (c2), the kit components (a), (b), and (c) exist as pastes. This has the advantage that a bone-cement paste can be produced by the user without a problem by mixing the different paste-like kit components. In particular, the disadvantages that arise during the mixing of components that exist in different aggregate states, for example, during the mixing of a powdery component and a fluid monomer component, are eliminated.

The kit components (a), (b), and (c) are adjusted to each other so that the individual components contained therein are present in precisely defined quantity ranges based on the total weight of the components contained in the kit components. According to the invention, total weight of the components contained in the kit components (a), (b), and (c) is understood to be the sum of the weights of the components contained in the kit components (a), (b), and (c).

According to the invention, the total weight percentage of a certain component, based on the total weight of the components contained in the kit components (a), (b), and (c), is understood to be the percentage of the total weight of the components contained in the kit components (a), (b), and (c) that is assumed by the sum of the weight percentages of the certain component contained in the kit components (a), (b), and/or (c).

If, for example, the total weight of the components of kit component (a) add up to 100 g, the total weight of the components of kit component (b) add up to 100 g, and the total weight of the components of kit component (c) add up to 100 g, then the total weight of the components contained in the kit components (a), (b), and (c) equals 300 g.

According to this example, if 30 g of filler (a2) is contained in kit component (a), 80 g of filler (b2) in kit component (b), and 40 g of filler (c2) in kit component (c), then the total weight of the fillers (a2), (b2), and (c2) equals 150 g. Accordingly, the total weight percentage of the fillers (a2), (b2), and (c2) in this example equals 50 weight percent, based on the total weight of the components contained in the kit components (a), (b), and (c).

The total weight percentage of the methacrylic acid esters (a1), (b1), and (c1) lies in the range of 15-50 weight percent, preferably 15-45 weight percent, and more preferred 20-45 weight percent, based on the total weight of the components contained in the kit components, preferably the kit components (a), (b), and (c).

The total weight percentage of the fillers (a2), (b2), and (c2) lies in the range of 40-85 weight percent, preferably 42-83 weight percent, more preferred 45-80 weight percent, and even more preferred 50-75 weight percent, based on the total weight of the components contained in the kit components, preferably the kit components (a), (b), and (c).

Due to this percentage of methacrylic acid esters (a1), (b1), and (c1), and fillers (a2), (b2), and (c2), after mixing of the components (a), (b), and (c), a paste is produced that is easy to work by the user, in particular easily shapeable.

The weight percentage of the radical initiator (a3) lies in the range of 0.01-4 weight percent, preferably in the range of 0.01-3 weight percent, more preferred in the range of 0.05-2.5 weight percent, and even more preferred in the range of 0.05-2 weight percent, based on the total weight of the components contained in the kit components, preferably the kit components (a), (b), and (c).

The weight percentage of the radical initiator (b3) lies in the range of 0.01-4 weight percent, preferably in the range of 0.01-3 weight percent, more preferred in the range of 0.05-2.5 weight percent, and even more preferred in the range of 0.05-2 weight percent, based on the total weight of the components contained in the kit components, preferably the kit components (a), (b), and (c).

The weight percentage of the accelerator (c3) lies in the range of 0.00001-4 weight percent, preferably 0.0001-3 weight percent, more preferred 0.001-3 weight percent, and even more preferred 0.05-2 weight percent, based on the total weight of the components contained in the kit components, preferably the kit components (a), (b), and (c).

The weight percentages of the radical initiator (a3), radical initiator (b3), and accelerator (c3) are not particularly critical. A content that is lower than the lower limits of the specified ranges leads to the result that the curing of the bone cement takes place more slowly without the use of additional polymerization aids. A content that is higher than the upper limits of the specified ranges leads to higher costs without significant added value.

The total weight percentage of the at least one halide salt lies in the range of 0.001-5 weight percent, preferably 0.005-4 weight percent, and more preferred 0.01-4 weight percent, based on the total weight of the components contained in the kit components, preferably the kit components (a), (b), and (c). A minimum content of halide salts of 0.001 weight percent, based on the total weight of the components contained in the kit components is required, so that the polymerization can be set in motion. A content of more than 5 weight percent, however, based on the total weight of the components contained in the kit components, has proven disadvantageous due to the toxicity of the halides.

The total weight of the at least one cross-linking agent lies in the range of 0.2-3 weight percent, preferably 0.5-2.75 weight percent, and even more preferred 1-2.5 weight percent, based on the total weight of the components (a), (b), and (c). The percentage of cross-linking agents in this range is essential, in order to impart a high impact strength to the cured bone cement. It has been shown that the impact strength of the cured bone cement is significantly reduced with a content of less than 0.2 weight percent and greater than 3 weight percent, each based on the total weight of the components contained in the kit components.

According to a preferred embodiment, the percentage of the composition contained in kit component (a) equals 20-40 weight percent, the percentage of the composition contained in kit component (b) equals 20-40 weight percent, and the percentage of the composition contained in kit component (c) equals 20-40 weight percent, based on the total weight of the compounds contained in kit components (a), (b), and (c).

According to the invention, the kit that contains at least the kit components (a), (b), and (c) is used for the production of bone cement. For this purpose, the at least three kit components (a), (b), and (c) are mixed with each other under formation of a paste. The mixture ratio preferably equals 0.5-1.5 weight parts of kit component (a), 0.5-1.5 weight parts of kit component (b), and 0.5-1.5 weight parts of kit component (c).

The mixing can be carried out with typical mixing devices, for example, a static mixer or a dynamic mixer.

After the mixing of the components of the kit, the resulting paste is adhesive-free according to the ISO 5833 standard and can be immediately worked.

The paste can be used, for example, for fixing joint endoprostheses or for filling bone defects. Both uses are known from the prior art in connection with conventional pastes.

The bone cement produced from the paste through curing attains its final strength approximately six to eight minutes after the mixing of the individual kit components.

The paste according to the invention contains at least one mono-functional, hydrophobic methacrylic acid ester (i). Any hydrophobic esters of the methacrylic acid can be used as the mono-functional, hydrophobic methacrylic acid ester (i).

Through the use of hydrophobic, mono-functional methacrylic acid esters (i), a later increase in volume of the bone cement and thus damage to the bone can be prevented. According to a preferred embodiment, the mono-functional methacrylic acid ester (i) is hydrophobic, if it has, besides the ester group, no additional polar groups. Preferably, the mono-functional, hydrophobic methacrylic acid ester (i) has no carboxyl groups, hydroxyl groups, amide groups, sulfonic acid groups, sulfate groups, phosphate groups, or phosphonate groups.

The methacrylic acid esters (i) used according to the invention preferably have a weight average molecular weight of less than 1000 g/mol.

The esters preferably comprise alkyl esters. According to a preferred embodiment, the alkyl esters are esters of methacrylic acid with alcohols having 1-20 carbon atoms, more preferred 1-10 carbon atoms, even more preferred 1-6 carbon atoms, and very especially preferred 1-4 carbon atoms. The alcohols can be substituted or unsubstituted and are preferably unsubstituted. The alcohols furthermore can be saturated or unsaturated and are preferably saturated. According to an especially preferred embodiment, the mono-functional, hydrophobic methacrylic acid ester (i) comprises methacrylic acid methyl ester or methacrylic acid ethyl ester.

Component (i) contains 15-50 weight percent, preferably 15-45 weight percent, and even more preferred 20-45 weight percent of at least one mono-functional, hydrophobic methacrylic acid esters (i) based on the total weight of the paste. Accordingly, the paste can contain one or more structurally different, mono-functional, hydrophobic methacrylic acid esters (i), as long as the total weight of the mono-functional, hydrophobic methacrylic acid esters (i) lies in the specified range.

According to the invention, the paste contains a filler (ii). The at least one filler (ii) contained in the paste comprises a material that is solid at room temperature and is capable of increasing the viscosity of the paste. The filler (ii) must be biocompatible.

According to a preferred embodiment, the filler (ii) is selected from the group consisting of (a) polymers soluble in at least the or one of the methacrylic acid esters (i), (b) polymers insoluble in at least the or one of the methacrylic acid esters (i), (c) inorganic salts, (d) inorganic oxides, (e) metals, and (f) metal alloys.

The polymer soluble in at least one of the methacrylic acid esters (i) preferably comprises a polymer having a weight average molecular weight of at least 150,000 g/mol. For example, the polymer can comprise a polymer or copolymer of a methacrylic acid ester. According to an especially preferred embodiment, the at least one polymer is selected from the group consisting of polymethacrylic acid methyl ester (PMMA), polymethacrylic acid ethyl ester (PMAA), polymethacrylic acid propyl ester (PMAP), polymethacrylic acid isopropyl ester, and polymethyl-co-acrylic methacrylate.

The polymer insoluble in at least one of the methacrylic acid esters (i) comprises, for example, polyethylene, polypropylene, or polybutadiene. The polymer soluble in at least one of the methacrylic acid esters (i) can be cross-linked or not cross-linked.

The inorganic salt usable as filler (ii) can be a salt soluble or insoluble in the methacrylic acid ester (i). Preferably, the inorganic salt comprises a salt of an element selected from the 2nd main group of the periodic table of the elements. According to a preferred embodiment, the inorganic salt is a salt of calcium, strontium, or barium. According to an especially preferred embodiment, the inorganic salt is calcium sulfate, barium sulfate, or calcium carbonate.

The inorganic oxide usable as filler (ii) can preferably comprise a metal oxide. According to a preferred embodiment, the inorganic oxide is an oxide of the transition metals. According to an especially preferred embodiment, the inorganic oxide comprises titanium dioxide or zirconium dioxide.

The metal usable as filler (ii) can comprise, for example, a transition metal. According to a preferred embodiment, the metal is tantalum or tungsten.

The metal alloy usable as filler (ii) is an alloy of at least two metals. Preferably, the alloy contains at least one transition metal. According to an especially preferred embodiment, the alloy contains at least tantalum or tungsten. The alloy can also comprise an alloy made of tantalum and tungsten.

The percentage of the at least one filler (ii) equals 40-85 weight percent, preferably 40-80 weight percent, and more preferred 45-75 weight percent, based on the total weight of the paste. Accordingly, the paste can contain one or more structurally different fillers (ii), as long as the total weight of the fillers (ii) lies in the specified range.

The paste further contains at least one radical initiator (iii) soluble in the at least one mono-functional, hydrophobic methacrylic acid ester (i) and has at least one peroxide group. As used herein, a radical initiator (iii) is understood to be a compound from which a radical can be formed by the action of the accelerator (v), wherein this radical is capable of triggering the polymerization of the at least one methacrylic acid ester (i). The radical initiator (iii) thus comprises a radical polymerization starter.

In the presence of the accelerator (v), the at least one radical initiator (iii) has a decomposition rate that is different from the radical initiator (iv). According to an especially preferred embodiment, in the presence of the accelerator (v), the radical initiator (iii) has a lower decomposition rate than the radical initiator (iv).

According to a preferred embodiment, the solubility of the at least one radical initiator (iii) in the at least one methacrylic acid ester (i) equals at least 0.5 weight percent, based on the weight of the at least one methacrylic acid ester (i). According to an especially preferred embodiment, the radical Initiator (iii) is selected from the group consisting of dibenzoyl peroxide and dilauroyl peroxide.

The paste contains 0.01-4 weight percent, preferably 0.01-3 weight percent, more preferred 0.05-2.5 weight percent, and even more preferred 0.05-2 weight percent of at least one radical initiator (iii), based on the total weight of the paste. Accordingly, the paste can contain one or more structurally different radical initiators (iii), as long as the total weight of the radical initiators (iii) lies in the specified range.

The paste also contains at least one radical initiator (iv) soluble in the at least one mono-functional, hydrophobic methacrylic acid ester (i) and has no peroxide groups. As used herein, the radical initiator (iv) is understood to be a compound from which a radical can be formed by the action of the accelerator (v), wherein this radical is capable of triggering the polymerization of the at least one methacrylic acid ester (i). The radical initiator (iv) thus comprises a radical polymerization starter.

In the presence of the accelerator (v), the at least one radical initiator (iv) has a decomposition rate that is different from radical initiator (iii). According to an especially preferred embodiment, in the presence of the accelerator (v), the radical initiator (iv) has a higher decomposition rate than the radical initiator (iii).

According to a preferred embodiment, the solubility of the at least one radical initiator (iv) in the at least one methacrylic acid ester (i) equals at least 0.5 weight percent, based on the weight of the at least one methacrylic acid ester (i).

The radical initiator (iv) preferably comprises barbituric acid or barbituric acid derivatives in which the barbituric acid carries a substituent on at least one of the positions 1 or 5.

According to the invention, the barbituric acid derivative is preferably mono-substituted. According to a preferred embodiment, a barbituric acid substituted at position 5 is used as the radical initiator (iv). The substituent of the barbituric acid derivative furthermore preferably comprises a hydrophobic substituent. Preferably, the barbituric acid derivative comprises an alkyl, cycloalkyl, or aryl derivative of the barbituric acid.

According to an especially preferred embodiment, the barbituric acid derivative is selected from the group consisting of cyclohexyl barbituric acid, 1,3,5-trimethyl barbituric acid, 1-phenyl-5-benzyl barbituric acid, 1-benzyl-5-phenyl barbituric acid, 1,3-dimethyl barbituric acid, 1,3-dimethyl-5-phenyl barbituric acid, 1-cyclohexyl-5-ethyl barbituric acid, 5-lauryl barbituric acid, 1-n-butyl-barbituric acid, 5-n-butyl barbituric acid, 5-allyl barbituric acid, 5-hydroxy-5-butyl barbituric acid, 5,5-dibromobarbituric acid, trichlorobarbituric acid, 5-nitrobarbituric acid, 5-aminobarbituric acid, 5-hydroxy barbituric acid, and 5,5-dihydroxy barbituric acid.

In one very especially preferred embodiment, the barbituric acid derivative is selected from the group consisting of 1-cyclohexyl-5-ethyl-barbituric acid, 1-n-butyl-barbituric acid, and 5-n-butyl-barbituric acid.

According to the invention, the term "barbituric acid derivatives" also includes alkaline earth salts and alkali salts of these barbituric acid derivatives.

The paste contains 0.01-4 weight percent, preferably 0.01-3 weight percent, more preferred 0.05-2.5 weight percent, and even more preferred 0.05-2 weight percent of at least one radical initiator (iv), based on the total weight of the paste. Accordingly, the paste can contain one or more structurally different radical initiators (iv), as long as the total weight of the radical initiator (iv) lies in the specified range.

The paste further contains at least one accelerator (v) soluble in the at least one methacrylic acid ester (i) and is capable of forming radicals from the radical initiators (iii) and (iv).

According to a preferred embodiment, the solubility of the accelerator (v) in the at least one methacrylic acid ester (i) equals at least 0.5 weight percent, based on the weight of the at least one methacrylic acid ester (i).

Accelerators that are capable of forming radicals from the radical initiators (iii) and (iv) are understood to be compounds that can convert the radical initiators (iii) and (iv) into radicals, optionally in the presence of additional compounds contained in the paste according to the invention, as for example halide ions. Such accelerators are well known from the prior art.

The accelerator (v) preferably comprises a salt having ions of metals that can assume, besides the oxidation stage 0, at least two additional oxidation stages. According to an especially preferred embodiment, the metal ions are selected from the group consisting of copper ions, iron ions, cobalt ions, and manganese ions. Accordingly, preferably an iron salt, a cobalt salt, or a manganese salt is used as the accelerator (v). According to a very especially preferred embodiment, the accelerator (v) is selected from the group consisting of copper(II)-2-ethylhexanoate, copper(II)-laurate, copper(II)-decanoate, copper(II)-octoate, copper(II) acetylacetonate, and copper (II)-methacrylate.

The paste contains 0.00001-4 weight percent, preferably 0.0001-3 weight percent, more preferred 0.001-3 weight percent, and even more preferred 0.05-2 weight percent of at least one accelerator (v), based on the total weight of the paste. Accordingly, the paste can contain one or more structurally different accelerators (v), as long as the total weight of the accelerator (v) lies in the specified range.

The paste also contains at least one halide salt (vi). The halide salt (vi) preferably comprises a halide salt soluble in the at least one methacrylic acid ester (i). According to a preferred embodiment, the solubility of the halide salt (vi) in the at least one methacrylic acid ester (i) equals at least 0.5 weight percent, based on the weight of the at least one methacrylic acid ester (i).

According to the invention, halide salts (vi) are understood to be salts that contain at least one type of halide ions and dissociate in the at least one methacrylic acid ester (i). Preferably, the halide ions comprise chloride ions or bromide ions, very preferred chloride ions. According to the invention, preferably metal halides, hydrochlorides, and quaternary ammonium halide salts can be used as the halide salts.

According to an especially preferred embodiment, the halide salt (vi) is selected from the group consisting of copper (II)-chloride, copper(II)-bromide, iron(III)-chloride, iron (III)-bromide, cobalt(II)-chloride, cobalt(II)-bromide, triethylamine hydrochloride, triethylamine hydrobromide, propylamine hydrochloride, butylamine hydrochloride, methacryloyl choline chloride, methyltrioctylammonium chloride, and triethyl benzyl ammonium chloride.

The percentage of the at least one halide salt (vi) equals 0.001-5 weight percent, preferably 0.005-4 weight percent, and more preferred 0.01-3 weight percent, based on the total weight of the paste. Accordingly, the paste can contain one or more structurally different halide salts (vi), as long as the total weight of the halide salts (vi) lies in the specified range.

The paste also contains at least one cross-linking agent (vii). As used herein, the cross-linking agent is understood to be a multi-functional compound capable of entering into covalent bonds with at least two monomer units that are different from each other. The cross-linking agent (vii) comprises a bi-functional or tri-functional compound. According to the invention the cross-linking agent should cause cross-linking of the polymerizing, mono-functional, hydrophobic methacrylic acid ester during the curing of the bone cement.

According to a preferred embodiment, the cross-linking agent (vii) has at least two acrylate groups. Especially preferred, the cross-linking agent (vii) is selected from the group consisting of ethylene glycol dimethacrylate, butylene glycol dimethacrylate (e.g., butane-1,4-diol-dimethacrylate) and hexamethylene dimethacrylate (e.g., hexane-1,6-diol-dimethacrylate).

The percentage of the at least one cross-linking agent (vii) equals 0.2-3 weight percent, preferably 0.5-2.75 weight percent, and more preferred 1-2.5 weight percent, based on the total weight of the paste. Accordingly, the paste can contain one or more structurally different cross-linking agents (vii), as long as the total weight of the cross-linking agents (vii) lies in the specified range.

In addition, the paste can also contain further components. These components can be selected, for example, from the group consisting of pharmaceutically active substances, radiopaque materials, dyes, and stabilizers. According to preferred embodiments, these comprise those pharmaceutically active substances, radiopaque materials, dyes, and/or stabilizers that were described above in connection with the kit.

The kit according to the invention or the paste according to the invention can preferably be used for fixing joint endoprostheses. For this purpose, preferably a paste is produced from the kit according to the invention and this is used analogously to the pastes known from the prior art for fixing joint endoprostheses.

Furthermore, the kit according to the invention or the paste according to the invention can also be used for filling bone defects. For this purpose, a paste is likewise preferably produced from the kit according to the invention and this is used analogously to the pastes known from the prior art for filling bone defects.

EMBODIMENT EXAMPLES

The monomers and the other chemicals used in Examples 1-3 were provided in pa. purity and were procured from the wholesale chemical trade.

Poly(methyl methacrylate)-co-methyl acrylate having a molecular weight of approximately 200,000 g/mol was used. This polymer is designated below for simplicity as PMMA. In addition, a poly(methyl methacrylate) cross-linked with ethylene glycol dimethacrylate was used, which is designated below as cross-linked PMMA. Aliquat 336 stands for methyltrioctylammonium chloride below.

The respective pastes of the kit components (a), (b), and (c) were produced, in a manner as follows: First, the methyl methacrylate was weighed in an inert plastic vessel. Then, the stabilizer and the respective initiator, or in (c) the accelerator, were dissolved in the methyl methacrylate while stirring at room temperature. Next, all of the other components were added. The resulting mixtures were then intensively mixed. Brushable pastes were thus formed.

Example 1

Kit 1

| Compositions | Methacrylic acid-ester | Fillers | Radical Initiator/Accelerator | Stabilizer |
| --- | --- | --- | --- | --- |
| Kit Component (a1) | 16.2 g Methyl methacrylate; 0.6 g Ethylene glycol dimethacrylate | 4.0 g Zirconium dioxide; 8.8 g PMMA; 9.2 g cross-linked PMMA; 0.4 g Methacrylamide | 0.8 g Dibenzoyl peroxide (75%) | 20 mg 2,6-Di-tert-butyl phenol |
| Kit Component (b1) | 16.2 g Methyl methacrylate, 0.6 g Ethylene glycol dimethacrylate | 4.0 g Zirconium dioxide; 8.8 g PMMA; 7.6 g cross-linked PMMA; 0.4 g Methacrylamide | 2.4 g 1-Cyclohexyl-5-ethyl-barbituric acid; 50 mg Aliquat 336 | 20 mg 2,6-Di-tert-butyl phenol |
| Kit Component (c1) | 16.2 g Methyl methacrylate, 0.6 g Ethylene glycol dimethacrylate | 4.6 g Zirconium dioxide; 8.6 g PMMA; 9.6 g cross-linked PMMA; 0.4 g Methacrylamide | 3 mg Copper(II)-2-ethylhexanoate | 20 mg 2,6-Di-tert-butyl phenol |

The kit components a1, b1, and c1 were mixed with each other intensively. A brushable cement paste was produced, which could be worked up to ca. 4 minutes and was cured after ca. 6 minutes. The cured cement was a white solid body.

Example 2

Kit 2

| Compositions | Methacrylic acid-ester | Fillers | Radical Initiator/Accelerator | Stabilizer |
| --- | --- | --- | --- | --- |
| Kit Component (a2) | 16.2 g Methyl methacrylate; 0.6 g Ethylene glycol dimethacrylate | 4.0 g Zirconium dioxide; 8.8 g PMMA; 9.2 g cross-linked PMMA; 0.4 g Methacrylamide | 0.8 g Dibenzoyl peroxide (75%) | 20 mg 2,6-Di-tert-butyl phenol |

| Compositions | Methacrylic acid-ester | Fillers | Radical Initiator/ Accelerator | Stabilizer |
|---|---|---|---|---|
| Kit Component (b2) | 16.2 g Methyl methacrylate, 0.6 g Ethylene glycol dimethacrylate | 4.0 g Zirconium dioxide; 8.8 g PMMA; 5.9 g cross-linked PMMA; 0.4 g Methacrylamide; 1.7 g Gentamicin sulfate (AK 610) | 2.4 g 1-Cyclohexyl-5-ethyl-barbituric acid; | 20 mg 2,6-Di-tert-butyl phenol |
| Kit Component (c2) | 16.2 g Methyl methacrylate, 0.6 g Ethylene glycol dimethacrylate | 4.6 g Zirconium dioxide; 8.8 g PMMA; 9.4 g cross-linked PMMA; 0.4 g Methacrylamide | 3 mg Copper(II)-2-ethylhexanoate; 50 mg Aliquat 336, 10 mg 2-Ethylhexanoic acid | 20 mg 2,6-Di-tert-butyl phenol |

The kit components a2, b2, and c2 were mixed with each other intensively. A brushable cement paste was produced, which could be worked for up to ca. 4 minutes and was cured after ca. 6 minutes. The cured cement was a white solid body.

With the kits of Examples 1 and 2, sample cement bodies (strips) with the dimensions 75 mm×10 mm×3.3 mm were produced. For determining the flexural strength and the impact strength (Dynstat method), sample cement bodies with dimensions 16 mm×10 mm×3.3 mm were produced. These sample bodies were stored 24 hours at 23° C. In addition, test bodies were stored in water for 24 hours at 37° C.

The 4-point flexural strength and the flexural modulus of the stored sample bodies were determined with the help of a Zwick universal testing machine.

| | | 4-Point Flexural Strength | |
|---|---|---|---|
| Examples | Storage Conditions | Flexural Strength [MPa] | Flexural Modulus [MPa] |
| Kit 1 | Air/23° C./24 hr | 58.2 ± 0.7 | 2374 ± 22 |
| Kit 1 | Water/37° C./24 hr | 72.8 ± 1.6 | 2632 ± 28 |
| Kit 2 | Air/23° C./24 hr | 57.2 ± 0.8 | 2250 ± 48 |
| Kit 2 | Water/37° C./24 hr | 59.8 ± 3.8 | 2286 ± 23 |

The flexural strength and the impact strength were determined with a Dynstat test apparatus.

| Example | Storage Conditions | Flexural Strength [MPa] | Impact Strength [kJ/m2] |
|---|---|---|---|
| Kit 1 | Air/23° C./24 hr | 89.6 ± 1.8 | 4.91 ± 0.27 |
| Kit 1 | Water/37° C./24 hr | 110.3 ± 2.7 | 4.49 ± 0.13 |
| Kit 2 | Air/23° C./24 hr | 76.8 ± 1.0 | 2.78 ± 0.08 |
| Kit 2 | Water/37° C./24 hr | 72.5 ± 1.1 | 2.58 ± 0.27 |

Example 3

The kit components described below were produced analogously to the preceding examples.

Kit Component (a)

| Compositions | Methacrylic acid-ester | Fillers | Radical Initiator | Stabilizer |
|---|---|---|---|---|
| A1 | 16.0 g Methyl methacrylate, 0.4 g Ethylene glycol dimethacrylate | 4.0 g Zirconium dioxide; 11.0 g PMMA; 7.7 g cross-linked PMMA; | 0.9 g Dibenzoyl peroxide (75%) | 20 mg 2,6-Di-tert-butyl phenol |
| A2 | 16.0 g Methyl methacrylate, 0.4 g Butane-1,4-diol-dimethacrylate | 4.0 g Zirconium dioxide; 11.0 g PMMA; 7.7 g cross-linked PMMA; | 0.9 g Dibenzoyl peroxide (75%) | 20 mg 2,6-Di-tert-butyl phenol |
| A3 | 16.0 g Methyl methacrylate, 0.4 g Hexane-1,6-dimethacrylate | 4.0 g Zirconium dioxide; 11.0 g PMMA; 6.2 g cross-linked PMMA; | 0.9 g Dibenzoyl peroxide (75%) | 20 mg 2,6-Di-tert-butyl phenol |
| A4 | 16.0 g Methyl methacrylate, 0.4 g Ethylene glycol dimethacrylate | 4.0 g Zirconium dioxide; 11.0 g PMMA; 6.2 g cross-linked PMMA; | 0.9 g Dibenzoyl peroxide (75%) | 40 mg 2,6-Di-tert-butyl phenol |

-continued

| Compositions | Methacrylic acid-ester | Fillers | Radical Initiator | Stabilizer |
|---|---|---|---|---|
| A5 | 16.0 g Methyl methacrylate, 0.4 g Butane-1,4-diol-dimethacrylate | 4.0 g Zirconium dioxide; 11.0 g PMMA; 6.2 g cross-linked PMMA; | 0.9 g Dibenzoyl peroxide (75%) | 40 mg 2,6-Di-tert-butyl phenol |
| A6 | 16.0 g Methyl methacrylate, 0.4 g Hexane-1,6-dimethacrylate | 4.0 g Zirconium dioxide; 11.0 g PMMA; 6.2 g cross-linked PMMA; | 0.9 g Dibenzoyl peroxide (75%) | 60 mg 2,6-Di-tert-butyl phenol |
| A7 | 16.0 g Methyl methacrylate, 0.4 g Ethylene glycol dimethacrylate | 4.0 g Zirconium dioxide; 11.0 g PMMA; 7.8 g cross-linked PMMA; | 0.8 g Dilauroly peroxide | 20 mg 2,6-Di-tert-butyl phenol |
| A8 | 14.0 g Methyl methacrylate, 0.4 g Ethylene glycol dimethacrylate | 4.0 g Zirconium dioxide; 11.0 g PMMA; 7.8 g cross-linked PMMA; | 0.8 g Dilauroly peroxide | 20 mg 2,6-Di-tert-butyl phenol |
| A9 | 16.0 g Methyl methacrylate, 0.4 g Hexane-1,6-dimethacrylate | 16.0 g Zirconium dioxide; 6.8 g PMMA; | 0.8 g Dilauroly peroxide | 20 mg 2,6-Di-tert-butyl phenol |
| A10 | 16.0 g Methyl methacrylate, 0.4 g Ethylene glycol dimethacrylate | 4.0 g Barium sulfate; 11.0 g PMMA; 7.7 g cross-linked PMMA; | 0.9 g Dibenzoyl peroxide | 20 mg 2,6-Di-tert-butyl phenol |
| A11 | 16.0 g Methyl methacrylate, 0.4 g Ethylene glycol dimethacrylate | 6.0 g Calcium carbonate; 11.0 g PMMA; 5.7 g cross-linked PMMA | 0.9 g Dibenzoyl peroxide | 20 mg 2,6-Di-tert-butyl phenol |
| A12 | 16.0 g Methyl methacrylate, 0.4 g Hexane-1,6-dimethacrylate | 4.0 g Tantalum powder; 11.0 g PMMA; 7.7 g cross-linked PMMA; | 0.9 g Dibenzoyl peroxide | 20 mg 2,6-Di-tert-butyl phenol |

Kit Components (b)

| Compositions | Methacrylic acid-ester | Fillers | Radical Initiator | Stabilizer |
|---|---|---|---|---|
| B1 | 16.0 g Methyl methacrylate, 0.4 g Ethylene glycol dimethacrylate | 4.0 g Zirconium dioxide; 11.0 g PMMA; 6.2 g cross-linked PMMA; | 2.4 g 1-Cyclohexyl-5-ethyl barbituric acid; 60 mg Aliquat 336 | 20 mg 2,6-Di-tert-butyl phenol |
| B2 | 16.0 g Methyl methacrylate, 0.4 g Butane-1,4-diol-dimethacrylate | 4.0 g Zirconium dioxide; 11.0 g PMMA; 6.2 g cross-linked PMMA; | 2.4 g 1-Cyclohexyl-5-ethyl barbituric acid; 60 mg Aliquat 336 | 20 mg 2,6-Di-tert-butyl phenol |
| B3 | 16.0 g Methyl methacrylate, 0.4 g Hexane-1,6-dimethacrylate | 4.0 g Zirconium dioxide; 11.0 g PMMA; 6.2 g cross-linked PMMA; | 2.4 g 1-Cyclohexyl-5-ethyl barbituric acid; 60 mg Aliquat 336 | 20 mg 2,6-Di-tert-butyl phenol |
| B4 | 16.0 g Methyl methacrylate, 0.4 g Ethylene glycol dimethacrylate | 4.0 g Zirconium dioxide; 11.0 g PMMA; 6.2 g cross-linked PMMA; | 2.4 g 1-Cyclohexyl-5-ethyl barbituric acid; 60 mg Aliquat 336 | 40 mg 2,6-Di-tert-butyl phenol |
| B5 | 16.0 g Methyl methacrylate, 0.4 g Butane-1,4-diol-dimethacrylate | 4.0 g Zirconium dioxide; 11.0 g PMMA; 6.2 g cross-linked PMMA; | 2.4 g 1-Cyclohexyl-5-ethyl barbituric acid; 60 mg Aliquat 336 | 40 mg 2,6-Di-tert-butyl phenol |

-continued

| Compositions | Methacrylic acid-ester | Fillers | Radical Initiator | Stabilizer |
|---|---|---|---|---|
| B6 | 16.0 g Methyl methacrylate, 0.4 g Hexane-1,6-dimethacrylate | 4.0 g Zirconium dioxide; 11.0 g PMMA; 6.2 g cross-linked PMMA; | 2.4 g 1-Cyclohexyl-5-ethyl barbituric acid; 60 mg Aliquat 336 | 60 mg 2,6-Di-tert-butyl phenol |
| B7 | 16.0 g Methyl methacrylate, 0.4 g Ethylene glycol dimethacrylate | 4.0 g Zirconium dioxide; 11.0 g PMMA; 6.2 g cross-linked PMMA; | 2.4 g 1-n-Butyl-5-n-butyl-barbituric acid; 60 mg Aliquat 336 | 20 mg 2,6-Di-tert-butyl phenol |
| B8 | 14.0 g Methyl methacrylate, 0.4 g Ethylene glycol dimethacrylate | 4.0 g Zirconium dioxide; 11.0 g PMMA; 8.2 g cross-linked PMMA; | 2.4 g 1-Cyclohexyl-5-ethyl barbituric acid; 60 mg Aliquat 336 | 20 mg 2,6-Di-tert-butyl phenol |
| B9 | 16.0 g Methyl methacrylate, 0.4 g Hexane-1,6-dimethacrylate | 16.0 g Zirconium dioxide; 5.2 g PMMA; | 2.4 g 1-Cyclohexyl-5-ethyl barbituric acid; 60 mg Aliquat 336 | 20 mg 2,6-Di-tert-butyl phenol |
| B10 | 16.0 g Methyl methacrylate, 0.4 g Ethylene glycol dimethacrylate | 4.0 g Barium sulfate; 11.0 g PMMA; 6.2 g cross-linked PMMA; | 2.4 g 1-n-Butyl-5-n-butyl-barbituric acid; 60 mg Aliquat 336 | 20 mg 2,6-Di-tert-butyl phenol |
| B11 | 16.0 g Methyl methacrylate, 0.4 g Ethylene glycol dimethacrylate | 6.0 g Calcium carbonate; 11.0 g PMMA; 4.2 g cross-linked PMMA; | 2.4 g 1-n-butyl-5-n-butyl-barbituric acid; 60 mg Aliquat 336 | 20 mg 2,6-Di-tert-butyl phenol |
| B12 | 16.0 g Methyl methacrylate, 0.4 g Hexane-1,6-dimethacrylate | 4.0 g Tantalum powder; 11.0 g PMMA; 6.2 g cross-linked PMMA; | 2.4 g 1-Cyclohexyl-5-ethyl barbituric acid; 60 mg Aliquat 336 | 60 mg 2,6-Di-tert-butyl phenol |
| B13 | 16.0 g Methyl methacrylate, 0.4 g Ethylene glycol dimethacrylate | 4.0 g Zirconium dioxide; 11.0 g PMMA; 4.6 g cross-linked PMMA; 1.6 g Gentamicin sulfate | 2.4 g 1-Cyclohexyl-5-ethyl barbituric acid; 60 mg Aliquat 336 | 20 mg 2,6-Di-tert-butyl phenol |
| B14 | 14.0 g Methyl methacrylate, 0.4 g Ethylene glycol dimethacrylate | 4.0 g Zirconium dioxide; 11.0 g PMMA; 8.2 g cross-linked PMMA; 5 mg Lissamine green, 5 mg 2-Ethyl-hexanoic acid | 2.4 g 1-Cyclohexyl-5-ethyl barbituric acid; 60 mg Aliquat 336 | 20 mg 2,6-Di-tert-butyl phenol |
| B15 | 14.0 g Methyl methacrylate, 0.4 g Ethylene glycol dimethacrylate | 4.0 g Zirconium dioxide; 11.0 g PMMA; 8.2 g cross-linked PMMA; 5 mg Lissamine green, 5 mg 2-Ethyl-hexanoic acid | 2.4 g 1-Cyclohexyl-5-ethyl barbituric acid; 60 mg Tetrabutyl ammonium chloride | 20 mg 2,6-Di-tert-butyl phenol |

Kit Components (c)

| Compositions | Methacrylic acid-ester | Fillers | Accelerator | Stabilizer |
|---|---|---|---|---|
| C1 | 16.0 g Methyl methacrylate, 0.4 g Ethylene glycol dimethacrylate | 4.0 g Zirconium dioxide; 11.0 g PMMA; 8.6 g cross-linked PMMA; | 3 mg Copper(II)-2-ethylhexanoate | 20 mg 2,6-Di-tert-butyl phenol |

-continued

| Compositions | Methacrylic acid-ester | Fillers | | Stabilizer |
|---|---|---|---|---|
| C2 | 16.0 g Methyl methacrylate, 0.4 g Butane-1,4-diol-dimethacrylate | 4.0 g Zirconium dioxide; 11.0 g PMMA; 8.6 g cross-linked PMMA; | 3 mg Copper(II)-2-ethylhexanoate | 20 mg 2,6-Di-tert-butyl phenol |
| C3 | 16.0 g Methyl methacrylate, 0.4 g Hexane-1,6-dimethacrylate | 4.0 g Zirconium dioxide; 11.0 g PMMA; 8.6 g cross-linked PMMA; | 3 mg Copper(II)-2-ethylhexanoate | 20 mg 2,6-Di-tert-butyl phenol |
| C4 | 16.0 g Methyl methacrylate, 0.4 g Ethylene glycol dimethacrylate | 4.0 g Zirconium dioxide; 11.0 g PMMA; 8.6 g cross-linked PMMA; | 2 mg Copper(II)-methacrylate | 40 mg 2,6-Di-tert-butyl phenol |
| C5 | 16.0 g Methyl methacrylate, 0.4 g Butane-1,4-diol-dimethacrylate | 4.0 g Zirconium dioxide; 11.0 g PMMA; 8.6 g cross-linked PMMA; | 2 mg Copper(II)-methacrylate | 40 mg 2,6-Di-tert-butyl phenol |
| C6 | 16.0 g Methyl methacrylate, 0.4 g Hexane-1,6-dimethacrylate | 4.0 g Zirconium dioxide; 11.0 g PMMA; 8.6 g cross-linked PMMA; | 2 mg Copper(II)-methacrylate | 60 mg 2,6-Di-tert-butyl phenol |
| | | | Radical Initiator | |
| C7 | 16.0 g Methyl methacrylate, 0.4 g Ethylene glycol dimethacrylate | 4.0 g Zirconium dioxide; 11.0 g PMMA; 8.6 g cross-linked PMMA; | 2 mg Copper(II)-acetylacetonate | 20 mg 2,6-Di-tert-butyl phenol |
| C8 | 14.0 g Methyl methacrylate, 0.4 g Ethylene glycol dimethacrylate | 6.0 g Zirconium dioxide; 11.0 g PMMA; 8.6 g cross-linked PMMA; | 2 mg Copper(II)-acetylacetonate | 20 mg 2,6-Di-tert-butyl phenol |
| C9 | 16.0 g Methyl methacrylate, 0.4 g Hexane-1,6-dimethacrylate | 16.0 g Zirconium dioxide; 7.6 g PMMA; | 2 mg Copper(II)-acetylacetonate | 20 mg 2,6-Di-tert-butyl phenol |
| C10 | 16.0 g Methyl methacrylate, 0.4 g Ethylene glycol dimethacrylate | 4.0 g Barium sulfate; 11.0 g PMMA; 8.6 g cross-linked PMMA; | 3 mg Copper(II)-2-ethylhexanoate | 20 mg 2,6-Di-tert-butyl phenol |
| C11 | 16.0 g Methyl methacrylate, 0.4 g Ethylene glycol dimethacrylate | 6.0 g Calcium carbonate; 11.0 g PMMA; 6.6 g cross-linked PMMA | 3 mg Copper(II)-2-ethylhexanoate | 20 mg 2,6-Di-tert-butyl phenol |
| C12 | 16.0 g Methyl methacrylate, 0.4 g Hexane-1,6-dimethacrylate | 4.0 g Tantalum powder; 11.0 g PMMA; 8.6 g cross-linked PMMA; | 3 mg Copper(II)-2-ethylhexanoate | 20 mg 2,6-Di-tert-butyl phenol |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A paste comprising:
   (i) 15-50 weight percent of at least one mono-functional, hydrophobic methacrylic acid ester,
   (ii) 40-85 weight percent of at least one filler,
   (iii) 0.01-4 weight percent of at least one radical initiator soluble in the methacrylic acid ester (i) and having at least one peroxide group,
   (iv) 0.01-4 weight percent of at least one radical initiator soluble in the methacrylic acid ester (i) and having no peroxide groups,
   (v) 0.000001-3 weight percent of at least one accelerator soluble in the methacrylic acid ester (i) and capable of forming radicals from the radical initiators according to (iii) and (iv), wherein the at least one accelerator is selected from the group consisting of copper(II)-laurate, copper(II)-decanoate, copper(II)-octoate, copper(II)-acetylacetonate, and copper(II)-methacrylate,
   (vi) 0.001-5 weight percent of at least one halide salt, and
   (vii) 0.2-3 weight percent of at least one cross-linking agent.

2. A method for fixing joint endoprostheses or filling bone defects, the method comprising applying the paste according to claim 1.

* * * * *